United States Patent
Beardsley

(10) Patent No.: US 9,693,827 B2
(45) Date of Patent: Jul. 4, 2017

(54) METHOD FOR SEALING A REUSABLE ELECTRICAL SURGICAL INSTRUMENT

(71) Applicant: Covidien LP, Mansfield, MA (US)

(72) Inventor: John W. Beardsley, Wallingford, CT (US)

(73) Assignee: Covidien LP, Mansfield, MA (US)

( * ) Notice: Subject to any disclaimer, the term of this patent is extended or adjusted under 35 U.S.C. 154(b) by 72 days.

(21) Appl. No.: 14/679,607

(22) Filed: Apr. 6, 2015

(65) Prior Publication Data
US 2015/0209110 A1    Jul. 30, 2015

Related U.S. Application Data

(63) Continuation of application No. 13/886,506, filed on May 3, 2013, now Pat. No. 9,015,919.

(51) Int. Cl.
| | | |
|---|---|---|
| *A61B 19/00* | (2006.01) | |
| *B21D 53/00* | (2006.01) | |
| *B29C 65/70* | (2006.01) | |
| *B29C 45/00* | (2006.01) | |
| *B29C 39/10* | (2006.01) | |
| *A61B 17/00* | (2006.01) | |

(Continued)

(52) U.S. Cl.
CPC .............. *A61B 19/00* (2013.01); *A61B 17/00* (2013.01); *A61B 90/00* (2016.02); *B21D 53/00* (2013.01); *B29C 39/10* (2013.01); *B29C 45/00* (2013.01); *B29C 65/70* (2013.01); *A61B 2017/00526* (2013.01); *A61B 2090/0813* (2016.02); *B29C 65/08* (2013.01); *B29C 65/483* (2013.01); *B29C 65/542* (2013.01); *B29C 65/562* (2013.01); *B29C 66/1142* (2013.01); *B29C 66/54* (2013.01); *B29L 2031/26* (2013.01); *B29L 2031/7546* (2013.01); *Y10T 29/49826* (2015.01); *Y10T 29/49893* (2015.01); *Y10T 29/49947* (2015.01); *Y10T 29/49966* (2015.01)

(58) Field of Classification Search
CPC .................................................. Y10T 428/195
USPC ............................................................ 428/60
See application file for complete search history.

(56) References Cited

U.S. PATENT DOCUMENTS

| 4,695,276 A | 9/1987 | Shinno et al. |
|---|---|---|
| 5,480,409 A | 1/1996 | Riza |

(Continued)

FOREIGN PATENT DOCUMENTS

| DE | 102011011215 A1 | 8/2012 |
|---|---|---|
| GB | 2115084 A | 9/1983 |

OTHER PUBLICATIONS

European Search Report dated Jul. 31, 2015, issued in European Application No. 14166883.

(Continued)

*Primary Examiner* — Alexander Thomas

(57) ABSTRACT

A method for sealing surgical instruments, particularly reusable electric surgical instruments sterilized using an autoclave process, is disclosed. The method having the steps of providing at least two body shells having a runner system on the mating surfaces, aligning the body shells, securing the body shells in position relative to each other, inserting an injection device into the runner system, injecting an elastomer material from the injection device into the runner system, removing the injection device from the runner system, and curing the elastomer material. The elastomer material seals the housing chamber of the instrument. The elastomer material may bond the body shells together.

6 Claims, 3 Drawing Sheets

(51) Int. Cl.

| | | |
|---|---|---|
| *A61B 90/00* | (2016.01) | |
| *B29L 31/00* | (2006.01) | |
| *B29C 65/08* | (2006.01) | |
| *B29C 65/48* | (2006.01) | |
| *B29C 65/54* | (2006.01) | |
| *B29C 65/56* | (2006.01) | |
| *B29C 65/00* | (2006.01) | |
| *B29L 31/26* | (2006.01) | |

(56) References Cited

U.S. PATENT DOCUMENTS

| | | |
|---|---|---|
| 5,601,601 A | 2/1997 | Tal et al. |
| 5,935,144 A | 8/1999 | Estabrook |
| 6,500,169 B1 | 12/2002 | Deng |
| 6,755,825 B2 | 6/2004 | Shoenman et al. |
| 7,237,990 B2 | 7/2007 | Deng |
| 9,015,919 B2 | 4/2015 | Beardsley |
| 2004/0099699 A1 | 5/2004 | Zubeck |
| 2004/0211668 A1 | 10/2004 | Montminy et al. |
| 2007/0027443 A1 | 2/2007 | Rose et al. |
| 2008/0308603 A1 | 12/2008 | Shelton et al. |

OTHER PUBLICATIONS

European Office Action dated Aug. 11, 2016, issued in European Application No. 14 166 883.

METHOD FOR SEALING A REUSABLE ELECTRICAL SURGICAL INSTRUMENT

CROSS-REFERENCE TO RELATED APPLICATION

This application is a continuation of U.S. patent application Ser. No. 13/886,506, filed May 3, 2013, now U.S. Pat. No. 9,015,919, the entire contents of which are hereby incorporated by reference.

BACKGROUND

Technical Field

The present disclosure relates generally to reusable surgical instruments, and more particularly, to reusable electrical surgical instruments that are sterilized.

Description of Related Art

Electrical surgical instruments generally comprise of a handle portion having multiple body shells, which houses the electrical components, and a working portion extending from the handle portion, which comes in contact with a patient. After each use, an electrical surgical instrument is disposed of, reused, or partially disposed of and partially reused. Any part of an electrical surgical instrument that is reused must be sterilized to neutralize potentially infectious agents before being reused.

The autoclave process has been used for many years to sterilized reusable surgical instruments. However, the steam and the high-pressure used in the autoclave process can damage electrical components within the housing. Even where the components are disposed in a shell, the components can be damaged if the steam is allowed to infiltrate the joints between the body shells of an electrical surgical instrument. Different sealing methods have been used to seal the joints between body shells.

One such sealing method is to bond the body shells of the handle portion together with adhesives. Another known method employs an o-ring that is compressed between the body shells using screws or other joining means.

The existing sealing methods are known to fail after a varying number of autoclave processes. One cause of the failure is that the sealing materials and the material of the body shells expand and contract at different rates and to differing extents during the autoclave process.

Based on the above, a continuing need exists for a sealing method that will extend the life of reusable electrical surgical instruments capable of maintaining a sealed chamber during the contracting and expansion that takes occurs during the autoclave process.

SUMMARY

Disclosed herein is a method for sealing body shells that injects an elastomer material into a runner system. The method includes the steps of providing body shells of an instrument having a runner system, aligning the body shells, securing the body shells together, inserting an injection device into the runner system, injecting an elastomer material, removing the injection device, and curing the elastomer material forming a seal between the body shells.

In an embodiment of the method, the runner system forms a half-cylindrical groove on the joining surface.

In a certain embodiment of the method, the runner system is on both joining surfaces of a pair of mutual joining surfaces.

In another embodiment of the method, the elastomer material forms a bond between the body shells along the pair of mutual joining surfaces.

DESCRIPTION OF THE DRAWINGS

The above and other aspects, features, and advantages of the present disclosure will become more apparent in light of the following detailed description when taken in conjunction with the accompanying drawings in which.

DETAILED DESCRIPTION OF THE EMBODIMENTS

Particular embodiments of the present disclosure will be described herein with reference to the accompanying drawings. In the following description, well-known functions or constructions are not described in detail to avoid obscuring the present disclosure in unnecessary detail.

Figure 1:
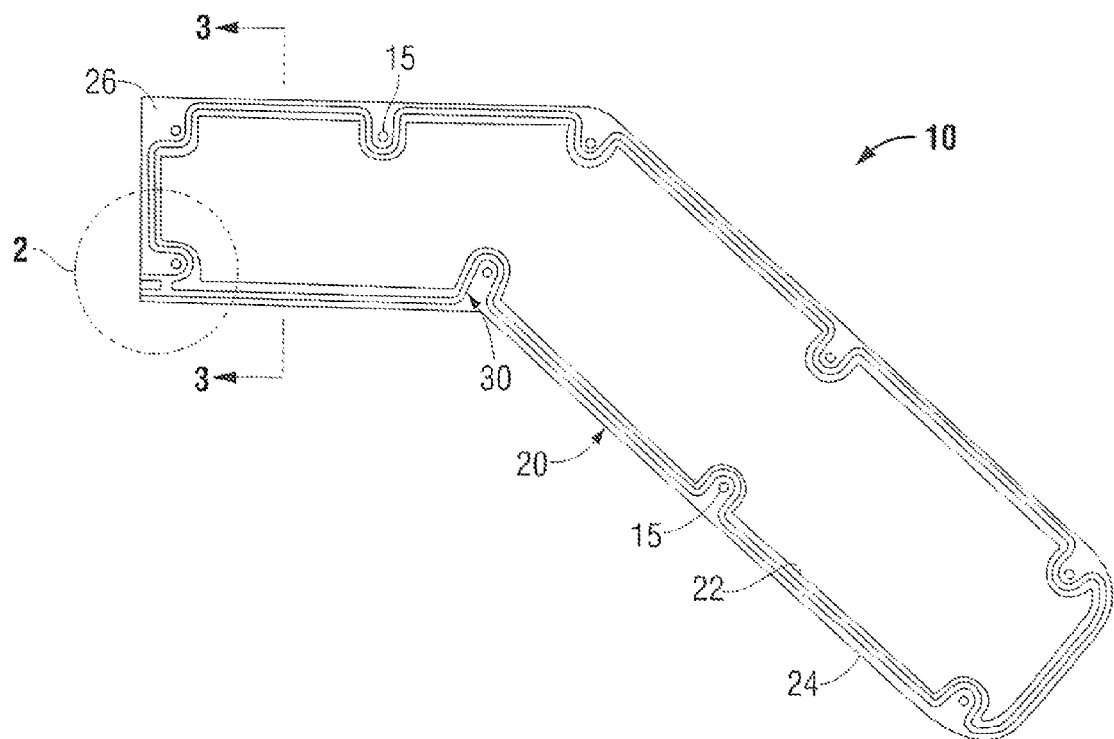
FIG. 1 is a top plan view of a body shell having a runner system on the joining surface.

Referring now to the drawings, in which like reference numerals identify identical or substantially similar parts throughout the several views, FIG. 1 illustrates first body shell 10 having runner system 30 in accordance with the principles of the present disclosure.

As shown in FIG. 1, first body shell 10 defines side wall 20 about the perimeter of first body shell 10. Side wall 20 has interior surface 22 and exterior surface 24. The side wall surface between interior surface 22 and exterior surface 24 defines joining surface 26. In any of the embodiments disclosed herein, the runner system can be a recess, channel, or space defined by part of the shell, and is generally narrow and extending the periphery of the chamber of the joined shell parts.

Figure 2:
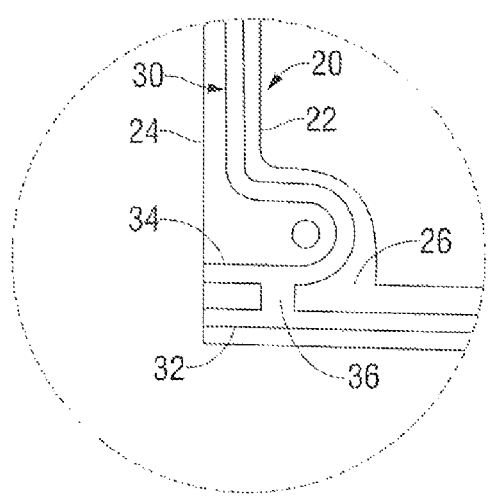
FIG. 2 is an enlarged view of the area of detail 2 of FIG. 1.

Continuing to refer to FIG. 1, runner system 30 is disposed on joining surface 26. Runner system 30 remains between interior surface 22 and exterior surface 24. Runner system 30 diverts around connecting holes 15. Runner system 30 has inlet port 32 and outlet port 34 connected by bridge section 36 as shown in FIG. 2. The corners of runner system 30 may be generally rounded.

Figure 4:
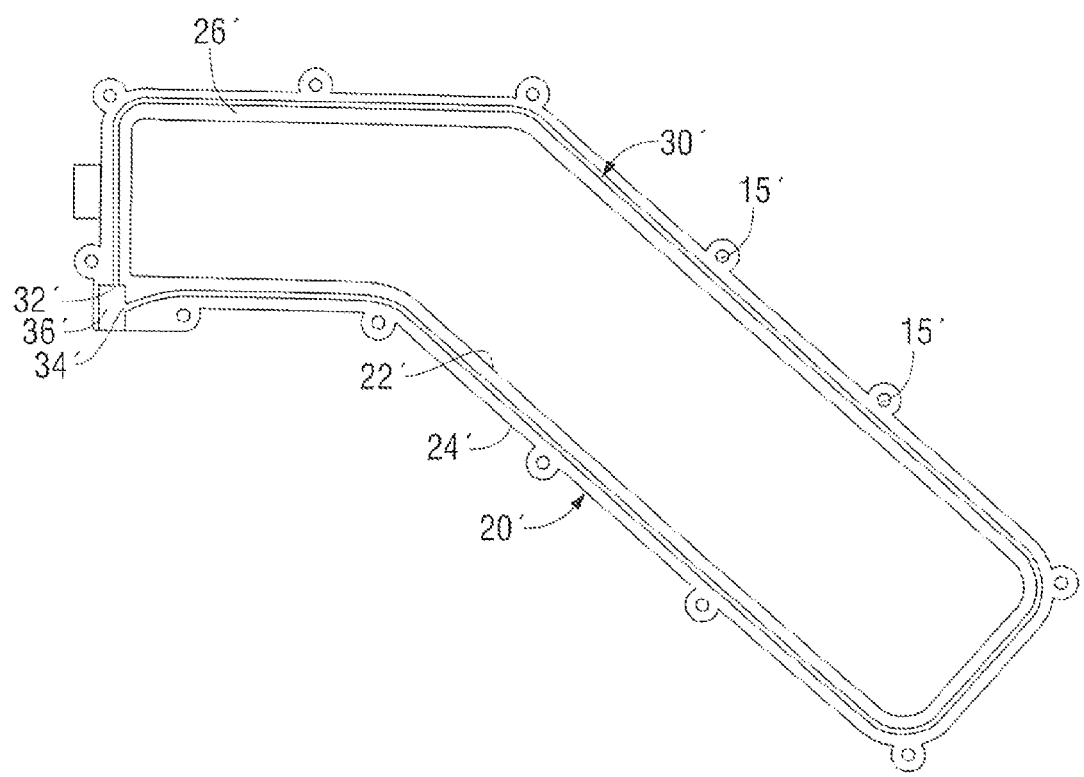
FIG. 4 is a top view of an alternative configuration of a runner system.

In the embodiment illustrated in FIG. 2, inlet port 32 and outlet port 34 each penetrate exterior surface 24 of side wall 20. In another embodiment, illustrated in FIG. 4, inlet port 32' and bridge 36' penetrate an exterior surface 24' of side wall 20' while outlet port 34' remains between interior surface 22' and exterior surface 24'.

Figure 3:
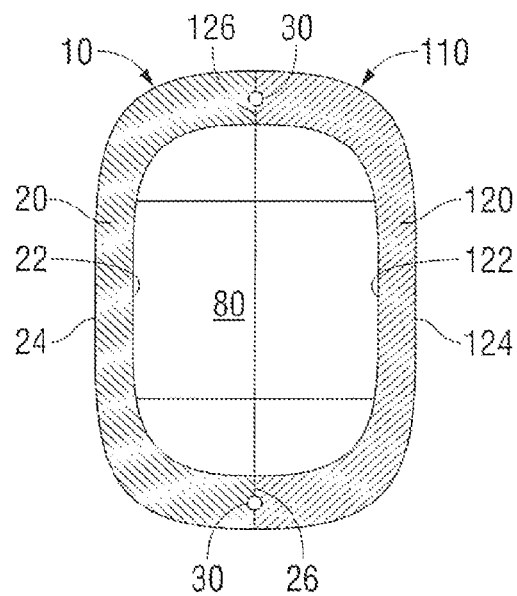
FIG. 3 is a front cross-sectional view of two body shells mated together taken along section line 3-3 of FIG. 1.

Now referring to FIGS. 1 and 3, a particular embodiment of the method is disclosed, the first step is to provide first body shell 10 and second body shell 110. First body shell 10 and second body shell 110 each having joining surfaces 26, 126. Joining surface 26 configured to mate with joining surface 126. The pair of joining surfaces 26, 126 defines a pair of mutual joining surfaces.

Runner system 30 is partially disposed within at least one of joining surfaces 26, 126. Runner system 30 may be partially disposed within each joining surface 26, 126. In this configuration, runner system 30 defines a substantially semi-circular groove on each joining surface 26, 126.

Next, the pair of mutual joining surfaces are aligned such that runner system 30 is in contact with each joining surface 26, 126 as shown in FIG. 3.

Once aligned, body shells 10, 110 are secured in position relative to one another. Any known method of securing the body shells together is envisioned. One known method is to clamp the body shells in position. Another known method is to screw the body shells together using connecting holes 15. Another known method is by sonic welding the body shells together. Adhesives and other methods can be used.

Figure 5:
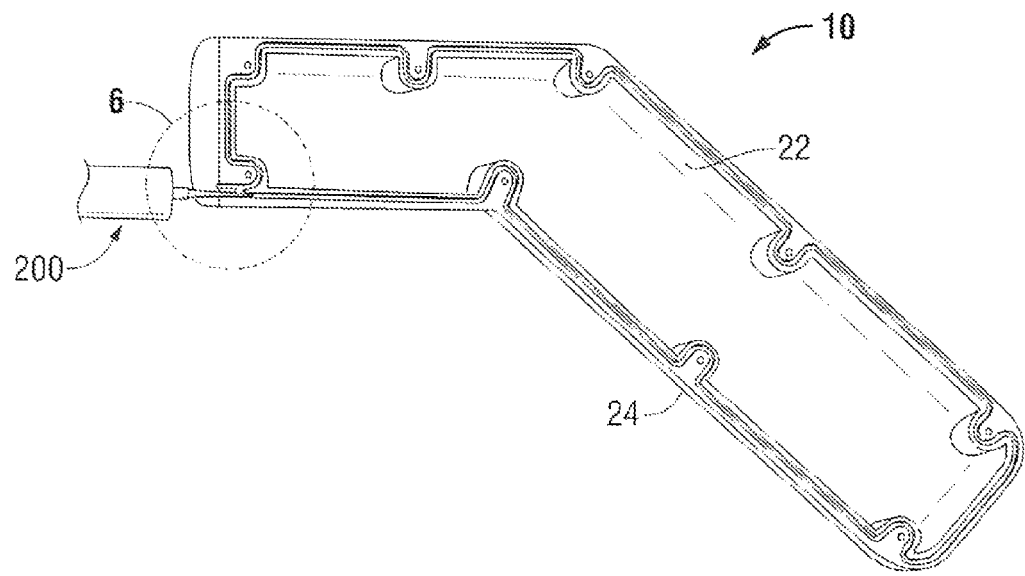
FIG. 5 is a top view of a body shell showing an injection device inserted in the runner system.
Figure 6:
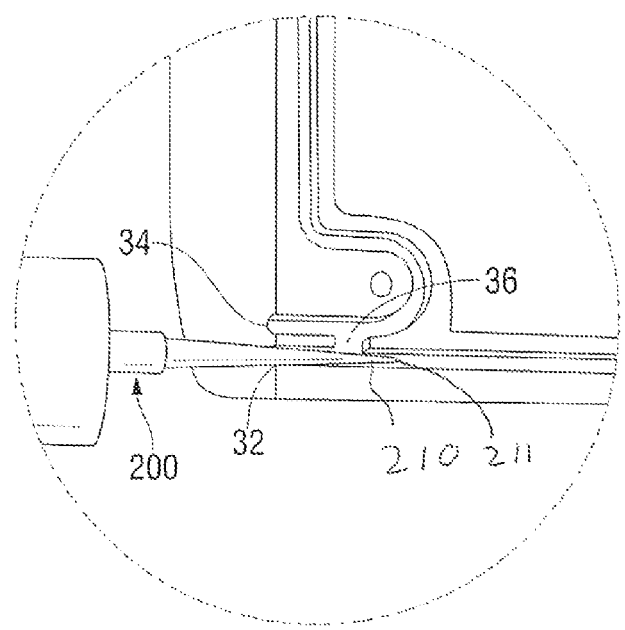
FIG. 6 is an enlarged view of the area of detail 6 of FIG. 5.

Once body shells 10, 110 are secured in position, injection device 200 is inserted into inlet port 32 such that tip 211 of injection device 200 is past bridge section 36 as shown in FIGS. 5 and 6. Injection device 200 includes distal portion 210 insertable into inlet port 32. Distal portion 210 includes a lumen in fluid communication with an opening in the tip 211 for delivering material. Distal portion 210 is fluidly coupled to a source of material (e.g., the elastomer material). The source can be a reservoir of elastomer material or a cartridge. Injection devices are well known to a person skilled in the art and include needles and other suitable devices.

After injection device 200 is inserted, an elastomer material (not shown) is injected from injection device 200 through tip 211 into inlet port 32. The Elastomer material may be a natural rubber, a synthetic rubber, a silicone that is room temperature vulcanizing (RTV), or any suitable material with the viscosity to flow through the runner system filling all voids before flowing from the outlet port.

When the elastomer material is injected through runner system 30, the elastomer material flows from inlet port 32 through runner system 30 towards outlet port 34. When the elastomer material flows from outlet port 34, injection device 200 is removed from inlet port 32 while continuing to inject the elastomer material. Injection device 200 is removed slowly to allow the elastomer material to fill outlet port 34 and bridge section 36. This is done to ensure that there are no voids in runner system 30. Thus, the elastomer material completely fills runner system 30.

When runner system 30 is filled with the elastomer material, the elastomer material is cured or allowed to cure. After the elastomer material is cured, the elastomer material forms a seal or barrier between exterior surfaces 24, 124 and interior surfaces 22, 122 forming housing chamber 80 within body shells 10, 110 illustrated in FIG. 3. The material may cure on its own, or using heat, UV light, etc.

In an embodiment of the method, the elastomer material also forms a bond between body shells 10, 110, further attaching the first and second body shells.

In any of the embodiments disclosed herein, the elastomer material has similar expansion and contracting properties to the materials of body shells 10, 110 such that during an autoclave process, the elastomer material and the body shell material expand and contract at substantially the same rate maintaining a barrier between housing chamber 80 and exterior surfaces 24, 124.

In any of the embodiments, runner system 30 is comprised of a half cylindrical groove in each joining surface 26, 126 such that when joining surfaces 26, 126 are aligned runner system 30 is substantially cylindrical, illustrated in FIG. 3.

It is envisioned that this method may be used for instruments with a plurality of body shells having a plurality of pairs of mutual joining surfaces having a plurality of runner systems. It is envisioned that each runner system may be injected either sequentially with respect to other runner systems or simultaneously with respect to other runner systems or a combination of sequential and simultaneous injection. In any of the embodiments disclosed herein, one or more chambers 80 can be formed so that components in the chambers are separately sealed from the exterior of the instrument, as well as each other.

While several embodiments of the disclosure have been shown in the drawings and/or discussed herein, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Different embodiments of the disclosure may be combined with one another based on the particular needs of the patients to achieve optimal results of the surgical procedures. Those skilled in the art will envision other modifications within the scope and spirit of the claims appended hereto.

What is claimed is:

1. A surgical instrument comprising:
   a first body shell having a first joining surface, the first joining surface defining a first runner system including a first groove that surrounds a perimeter of the first joining surface, an inlet port, an outlet port, and a bridge section, separate from the first groove, that fluidly connects the inlet and outlet ports; and
   a second body shell having a second joining surface adapted to mate with the first joining surface.

2. The surgical instrument according to claim 1, wherein the first runner system is configured to receive a fluid that seals the surgical instrument along the first and second joining surfaces.

3. The surgical instrument according to claim 1, wherein the first runner system is configured to receive a fluid that secures the first and second joining surfaces together.

4. The surgical instrument according to claim 1, wherein the second joining surface defines a second runner system including a second groove that surrounds a perimeter of the second joining surface and that mirrors the first groove.

5. The surgical instrument according to claim 1, wherein the inlet port is adjacent the outlet port.

6. The surgical instrument according to claim 1, wherein a first end of the first groove terminates at the inlet port and a second end of the first groove terminates at the outlet port.

* * * * *